US007449292B2

(12) United States Patent
Liggett et al.

(10) Patent No.: US 7,449,292 B2
(45) Date of Patent: *Nov. 11, 2008

(54) METHODS FOR PREDICTING RELATIVE EFFICACY OF A BETA BLOCKER THERAPY BASED ON A B1-ADRENERGIC RECEPTOR POLYMORPHISM

(75) Inventors: Stephen Bryant Liggett, Cincinnati, OH (US); Lynne Elizabeth Wagoner, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 165 days.

This patent is subject to a terminal disclaimer.

(21) Appl. No.: 10/941,063

(22) Filed: Sep. 13, 2004

(65) Prior Publication Data

US 2005/0112632 A1    May 26, 2005

Related U.S. Application Data

(60) Provisional application No. 60/502,837, filed on Sep. 12, 2003.

(51) Int. Cl.
*C12Q 1/68* (2006.01)
*C07H 21/02* (2006.01)
*C07H 21/04* (2006.01)
*C12P 19/34* (2006.01)
*C07K 14/435* (2006.01)
*G01N 33/53* (2006.01)

(52) U.S. Cl. .......................... 435/6; 435/7.1; 435/91.2; 536/23.5; 536/24.31; 530/350; 530/395

(58) Field of Classification Search ........................ None
See application file for complete search history.

(56) References Cited

U.S. PATENT DOCUMENTS

| | | | |
|---|---|---|---|
| 4,873,191 A | 10/1989 | Wagner et al. | |
| 4,965,188 A | 10/1990 | Mullis et al. | |
| 5,002,867 A | 3/1991 | Macevicz | |
| 5,130,238 A | 7/1992 | Malek et al. | |
| 5,169,766 A | 12/1992 | Schuster et al. | |
| 5,202,231 A | 4/1993 | Drmanac et al. | |
| 5,302,509 A | 4/1994 | Cheeseman | |
| 5,679,524 A | 10/1997 | Nikiforov et al. | |
| 6,365,618 B1 * | 4/2002 | Swartz | 514/11 |
| 2002/0187491 A1 * | 12/2002 | Johnson | 435/6 |
| 2003/0113725 A1 | 6/2003 | Small et al. | |
| 2003/0143608 A1 * | 7/2003 | Filigheddu et al. | 435/6 |

FOREIGN PATENT DOCUMENTS

| | | |
|---|---|---|
| EP | 329822 | 6/1994 |
| WO | WO88/10315 | 12/1988 |
| WO | WO89/06700 | 7/1989 |
| WO | WO89/10414 | 11/1989 |
| WO | WO90/01069 | 2/1990 |
| WO | WO90/09455 | 8/1990 |
| WO | WO91/02087 | 2/1991 |
| WO | WO92/15712 | 9/1992 |
| WO | WO94/03630 | 2/1994 |
| WO | WO95/17676 | 6/1995 |
| WO | WO 01/11039 A2 | 2/2001 |

OTHER PUBLICATIONS

Perez et al. Nature Medicine. Sep. 14, 2003, 9: 1300-1305.*
Small et al. Methods in Enzymology. 2002. 343: 459-475.*
Liu et al. Clinical Pharmacology & Therapeutics. 2003. 74:372-379.*
Mason, Moore, Green and Liggett, "A Gain-of-Function Polymorphism in a G-protein Coupling Domain of the Human $\beta_1$ Adrenergic Receptor," *J. Biol. Chem.* 274 (18), pp. 12670-12674 (1999).
Small, Wagoner, Levin, Kardia and Liggett, "Synergistic Polymorphisos of $\beta_1$ and $\alpha_{2C}$- Adrenergic Receptors and the Risk of Congestive Heart Failure," *New Engl. J. of Med.* 347:1135-1142 (Oct. 10, 2002).
De Boer, R. A., et al., "Polypharmacy in Chronic Heart Failure: Practical Issues Regarding the Use of Angiotensin-Converting Enzyme Inhibitors, Beta-Blockers and Other Drugs," European Society of Cardiology, European Heart Journal Supplements, Apr. 2002, pp. D111-D116, vol. 4, Supplement D.
Kass, D. A., "β-Receptor Polymorphisms: Heart Failure's Crystal Ball," Nature Medicine, Oct. 2003, pp. 1260-1262, vol. 9, No. 10.
Maqbool, A., et al., "Common Polymorphisms of $\beta_1$-Adrenoceptor: Identification and Rapid Screening Assay," The Lancet, Mar. 13, 1000, pp. 897, vol. 353, No. 9156, Lancet Limited, London, GB.
Perez, J. M., et al., "$\beta_1$-Adrenergic Receptor Polymorphisms Confer Differential Function and Predisposition to Heart Failure," Nature Medicine, pp. 1300-1305, vol. 9, No. 10.
Sofowora G. G., "A Common $\beta_1$-Adrenergic Receptor Ploymorphism (Arg389Gly) Affects Blood Pressure Response to $\beta_1$ Blockade," Clinical Pharmacology & Therapeutics, Apr. 2003, pp. 366-371, vol. 73, No. 4, Mosby-Year Book St. Louis, MO.
Tesson, F., et al., "Characterization of a Unique Genetic Variant in the $\beta_1$-Adrenoceptor Gene and Evaluation of its Role in Idiopathic Dilated Cardiomyopathy," Journal of Molecular and Cellular Cardiology, May 1999, pp. 1025-1032, vol. 31.

(Continued)

*Primary Examiner*—Carla Myers
(74) *Attorney, Agent, or Firm*—Fenwick & West LLP

(57) ABSTRACT

Methods and compositions for the detection, diagnosis, and prevention of cardiac conditions are provided. Polymorphisms of $\beta_1$-adrenergic receptor are provided. The Gly389 $\beta_1$-adrenergic receptor variants are not as responsive to treatment $\beta$ blockers such as carvedilol, metoprolol or bisoprol. Thus, genotyping $\beta_1$-adrenergic receptor polymorphisms is useful for predicting relative responsiveness to treatment with beta blockers. The Gly389 polymorphism also may be used, alone or in conjunction with other adrenergic receptor polymorphisms, to predict relative risk of developing cardiovascular diseases such as heart failure or to predict relative survival rate in patients with heart failure or other cardiovascular diseases. Also provided are transgenic mice and transgenic cells expressing the $\beta_1$-adrenergic receptor polymorphisms, and their use in identifying therapeutic agents.

8 Claims, 3 Drawing Sheets

OTHER PUBLICATIONS

Wagoner, L. E., et al., "Polymorphisms of the $\beta_1$-Adrenergic Receptor Predict Exercise Capacity in Heart Failure," American Heart Journal, Nov. 2002, pp. 840-846, vol. 144, No. 5.
Givertz, M.M. Underlying causes and survival in patients with heart failure. N. *Engl. J. Med.* 342, 1 120-1 122 (2000).
van Campen, L.C., Visser, F.C. & Visser, C.A. Ejection fraction improvement by beta-blocker treatment in patients with heart failure: an analysis of studies published in the literature. *J. Cardiovasc. Pharmacol.* Suppl 1, S31-S35 (1998).
Franz, W.-M., Müller, O.J. & Katus, H.A. Cardiomyopathies: from genetics to the prospect of treatment. *Lancet* 358, 1627-1637 (2001).
Engelhardt, S., Hein, L., Wiesmann, F. & Lohse, M.J. Progressive hypertrophy and heart failure in beta 1 -adrenergic receptor transgenic mice. *Proc. Natl. Acad. Sci. U.S.A.* 96, 7059-7064 (1999).
Liggett, S.B. $\beta$-adrenergic receptors in the failing heart: the good, the bad, and the unknown. *J. Clin. Invest.* 107, 947-948 (2001).
Mason, D.A., Moore, J.D., Green, S.A. & Liggett, S.B. A gain-of-function polymorphism in a G-protein coupling domain of the human $\beta_1$ adrenergic receptor. *J. Biol. Chem.* 274, 12670-12674 (1999).
Moore, J.D., mason, D.A., Green, S.A., Hsu, J. & Liggett, S.B. Racial differences in the frequencies of cardiac $\beta_1$-adrenergic receptor polymorphisms: analysis of c145A>G and c1165G>C. *Hum. Mutat. Mutation and Polymorphism Report #56 Online.* Citation also in print *Hum. Mutat.* 14, 271-271 (1999).
Palczewski, K. et al. Crystal structure of rhodopsin: A G protein-coupled receptor. *Science* 289, 739-745 (2000).
Wagoner, L.E. et al. Polymorphisms of the $\beta_1$-adrenergic receptor predict exercise capacity in heart failure. *Am. Heart J* 144, 840-846 (2002).
Bengtsson, K. et al. Polymorphism in the $\beta_1$-adrenergic receptor gene and hypertension. *Circ.* 104, 187-190 (2001).
D'Angelo, D.D. et al., Transgenic G$\alpha$q overexpression induces cardiac contractile failure in mice. *Proc. Natl. Acad. Sci. U. S. A.* 94, 8121-8126 (1997).
Liggett, S.B. et al. Early and delayed consequences of $\beta_1$-adrenergic receptor overexpression in mouse hearts. *Circ.* 101, 1707-1714 (2000).
Bristow, M.R. et al. Decreased catecholamine sensitivity and $\beta_1$-adrenergic-receptor density in failing human hearts. N. *Engl, J. Med.* 307, 205-211 (1982).
Bristow, M.R., Hershberger, R.E., Port, J.D., Minobe, W. & Rasmussen, R. $\beta_1$- and $\beta_2$-adrenergic receptor-mediated adenylate cyclase stimulation in nonfailing and failing human ventricular myocardium. *Mol. Pharmacol.* 35, 295-303 (1988).
Dunigan, C.D. Hoang, Q., Curran, P.K. & Fishman, P.H. Complexity of agonist- and cyclic AMP-mediated downregulation of the human $\beta_1$-adrenergic receptor: role of internalization, degradation, and mRNA destabilization. *Biochm.* 41, 8019-8030 (2002).
Dorn, G.W.I., Tepe, N.M., Wu, G., Yatani, A. & Liggett, S.B. Mechanisms of impaired $\beta$ adrenergic receptor signaling in G$_{\alpha q}$-mediated cardiac hypertrophy and ventricular dysfunction. *Mol. Pharmacol.* 57, 278-287 (2000).
Bohm, M. et al. Desensitization of adenylate cyclase and increase of Gi alpha in cardiac hypertrophy due to acquired hypertension. *Hypertension* 20, 103-112 (1992).
Ungerer, M., Bohm, M., Elce, J.S., Erdrnann, E. & Lohse, M.J. Altered expression of beta-adrenergic receptor kinase and beta 1-adrenergic receptors in the failing human heart, *Circ.* 87, 454-463 (1993).
Bohm, M. et al. Increase of Gi alpha in human hearts with dilated but not ischemic cardiomyopathy, *Circ.* 82, 1249-1265 (1990).
Eschenhagen, T. et al. Increased messenger RNA level of the inhibitory G protein $\alpha$ subunit G$_{i\alpha-2}$ in human end-stage heart failure. *Circ. Res.* 70, 688-696 (1992).
Packer, M. et al. Effect of carvedilol on the morbidity of patients with severe chronic heart failure: results of the carvedilol prospective randomized cumulative survival (COPERNICUS) study. *Circ.* 106, 2194-2199 (2002).
Bristow, M.R. et al. $\beta_1$-and $\beta_2$-adrenergic-receptor subpopulations in nonfailing and failing human ventricular myocardium: coupling of both receptor subtypes to muscle contraction and selective $\beta_1$-receptor downregulation in heart failure. *Circ. Res.* 59, 297-309 (1986).
Rathz, D.A., Gregory, K.N., Fang, Y ., Brown, K.M. & Liggett, S.B. Hierarchy of polymorphic variation and desensitization permutations relative to $\beta_1$-and $\beta_2$-adrenergic receptor signaling. *J. Biol. Chem.* 278, 10784-10789 (2003).
Yussman, M.G. et al. Mitochondrial death protein Nix is induced in cardiac hypertrophy and triggers apoptotic cardiomyopathy. *Nat. Med.* 8, 725-730 (2002).
Serikov, V.B., Petrashevskaya, N.N., Canning, A.M. & Schwartz, A. Reduction of [Ca$_{2+}$]i restores uncoupled beta-adrenergic signaling in isolated perfused transgenic mouse hearts. *Circ. Res.* 88, 9-11 (2001).
Tepe, N.M. et al. Altering the receptor-effector ratio by transgenic overexpression of type V adenylyl cyclase: enhanced basal catalytic activity and function without increased cardiomyocyte $\beta$-adrenergic signalling. *Biochem.* 38, 16706-16713 (1999).
Small, K.M., Rathz, D.A. & Liggett, S.B. Identification of adrenergic receptor polymorphisms. *Methods Enzymol*, 343, 459-475 (2002).
Wagoner, L.E. et al. Polymorphisms of the $\beta_2$-adrenergic receptor determine exercise capacity in patients with heart failure. *Circ. Res.* 86, 834-840 (2000).
H. G. Dohlman et al., Annu. Rev. Biochem. 60:653-688 (1991).
J. R. Carstairs et al., Am. Rev. Respir. Dis. 132:541-547 (1985).
Q. A. Hamid et al., Eur. J. Pharmocol. 206:133-138 (1991).
T. Frielle et al., Proc. Natl. Acad. Sci. (USA) 84:7920-7924 (1987).
T.L. Yang-Feng et al., Proc. Natl. Acad. Sci. (USA) 87: 1516-1520 (1990).
W. H. Berrettini, et al., Nucl. Acids Res. 16:7754 (1988).
B. K. Kobilka et al., Proc. Natl. Acad. Sci. (USA) 84:46-50 (1987).
E. Reihsaus et al., *Am.* J. Resp. Cell. Mol. Biol. 8:334-339 (1993).
K.-U. Lentes et al., Nucleic Acids Res. 16:2359 (1988).
C. K. McQuitty et al., Hum. Genet. 93:225 (1994).
K. J. Holroyd et al., *Am.* J. Respir. Crit. Care med. (Abstract) 151:A673 (1995).
D. M. Cooper et al., *Am.* J. Respir. Crit. Care med. (Abstract) 153:A254 (1996).
K. S. Tan et al., *Am.* J. Respir. Crit. Care Med. (Abstract) 155:A208 (1997).
J. Turki et al., J. Clin. Invest. 95:1635-1641 (1995).
I. P. Hall et al., The Lancet 345: 1213-1214 (1995).
J. C. Dewar et al., J. Allergy Clin. Imm. (In Press) Aug. 1997; 100(2):261-5.
S. A. Green et al., J. Biol. Chem. 268:23116-23121 (1993).
S. A. Green et al., Biochemistry 33:9414-9419 (1994).
J. Turki et al., Proc. Natl. Acad. Sci. (USA) 93: 10483-10488.
S. A. Green et al., Am. J. Respir. Cell Mol. Biol. 13:25-33 (1995).
M. R. Bristow et al., Mol. Pharmacol. 35:295-303 (1988).
O.E. Brodde et al., J. cardiovasc. Pharmacol. 8:1235-1242 (1986).
M. R. Bristow et al., Circ. Res. 59:297-309 (1986).
P. Arner Am. J. Clin. Nutr. 55:228S-236S (1992).
S. Reynisdottir et al., Diabetologia 37:428-435 (1994).
L. E. Wagoner et al., Circulation 94:8(Abstract) (Oct. 15, 1996).
Higashi, et al. Biochem. Biophys. Res. Comm. 232:728-730 (1997).
S. Krief et al., J. Clin. Invest. 91:344-349 (1993).
N. J. Rothwell et al., Nature 281:31-35 (1979).
P. Trayhurn et al., Biochem. Soc. Trans. 14:236-239 (1986).
B. Lowell et al., J. Clin. Invest. 95:923 (1995).
J. Himms-Hagen et al., Am. J. Physiol. 266:1371-1382 (1994).
S. Tsujii et al, Brain Res. 587:226-232 (1992).
T. Yoshida et al., Life Sciences 54:491-498 (1994).
J. F. Gusella Ann. Rev. Biochem. 55:831-854 (1986).
Sakai et al., Nucl. Acids. Res. 86:6230-6234 (1989).
Komher, J. S. et al., Nucl. Acids. Res. 17:7779-7784 (1989).
Sokolov, B. P., Nucl. Acids Res. 18:3671 (1990).
Syvanen, A.-C., et al., Genomics 8:684-692 (1990).
Kuppuswamy, M. N. et al., Proc. Natl. Acad. Sci. (U.S.A.) 88:1143-1147 (1991).
Prezant, T. R. et al., Hum. Mutat. 1:159-164 (1992).
Ugozzoli, L. et al., GATA 9: 107-112 (1992).
Nyren, P. et al., Anal. Biochem. 208:171-175 (1993).
Syvanen, A.-C., et al., Amer. J. Hum. Genet. 52:46-59 (1993).
Barany, F., Proc. Natl. Acad. Sci. (U.S.A.) 88: 189-193 (1991).
Landegren, U. et al., Science 241:1077-1080 (1988).

Nickerson, D. A. et al., Proc. Natl. Acad. Sci. (U.S.A.) 87:8923-8927 (1990).

Wu, D. Y. et al., Genomics 4:560-569 (1989).

Kwoh, D. et al., Proc. Natl. Acad. Sci. (U.S.A.) 86:1173-1177 (1989).

Walker, G. T. et al., Proc. Natl. Acad. Sci. (U.S.A.) 89:392-396 (1992).

M. Orita et al., Genomics 5:874-879 (1989).

R.M. Wartell et al., Nucl. Acids Res. 18:2699-2706 (1990).

White, H.L., De Boer, R.A., Maqbool, A., Greenwood, D., van Veldhuisen, D.J., Cuthbert, R., Ball, S.G., Hall, A.S., and Balmforth, A.J. 2003. An evaluation of the $\beta_1$-adrenergic receptor Arg389Gly polymorphism in individuals with heart failure: a MERIT-HF substudy. *Eur. J. Heart Failure* 5:463-468.

\* cited by examiner

METHODS FOR PREDICTING RELATIVE EFFICACY OF A BETA BLOCKER THERAPY BASED ON A B1-ADRENERGIC RECEPTOR POLYMORPHISM

CROSS-REFERENCE TO RELATED APPLICATIONS

This application claims priority from U.S. Ser. No. 60/502,837, filed on Sep. 12, 2003, which is incorporated herein by reference in its entirety.

GOVERNMENT INTEREST

This invention was made with support of government grant HL52318 from the National Institutes of Health. Therefore, the United States government may have certain rights in the invention.

FIELD OF INVENTION

The present invention provides methods and compositions for diagnosing and treating cardiovascular diseases, such as heart failure. The invention further provides for the use of β-adrenergic receptor gene polymorphism in the diagnosis, prognosis, and treatment selection for cardiovascular diseases, obesity, and diabetes.

BACKGROUND OF THE INVENTION

The mortality in heart failure is high, with ~50% of patients dying within 5 years of diagnosis. One of the most promising treatments for heart failure is administration of β-adrenergic receptor antagonists (often called "β-blockers").

There are at least nine sub-types of adrenergic receptors (H. G. Dohlman et al., *Annu. Rev. Biochem.* 60:653-688 (1991); S. B. Liggett et al., In: Catecholamines, Bouloux, ed. W. B. Sounders, London (1993)), of which at least three sub-types are β-adrenergic receptors, namely $\beta_1$-, $\beta_2$-, and $\beta_3$-adrenergic receptors. These beta adrenergic receptors (β-AR) bind to endogenous catecholamines, epinephrine (adrenaline) and norepinephrine (noradrenaline).

The $\beta_1$- and $\beta_2$-adrenergic receptors ($\beta_1$-AR and $\beta_2$-AR) are expressed in many organs in the body, including heart, lung, vascular tissue, and pancreas (S. B. Ligget In: The Lung: Scientific Foundations, R. G. Crystal et al. (ed.) Lippincott-Raven Publishers, Philadelphia (1996); J. R. Carstairs et al., *Am. Rev. Respir. Dis.* 132:541-547 (1985); Q. A. Hamid et al., *Eur. J. Pharmacol.* 206:133-138 (1991)). In the heart, one or both of these receptors regulate heart rate and pumping function. In addition, these receptors mediate the actions of adrenaline and noradrenaline, as well as a host of synthetic agonists as well.

Both $\beta_1$-AR and $\beta_2$-AR have been cloned and sequenced (T. Frielle et al., *Proc. Natl. Acad. Sci.* (USA) 84:7920-7924 (1987) and B. K. Kobilka et al., *Proc. Natl. Acad. Sci.* (USA) 84:46-50 (1987)). The $\beta_1$-AR gene has been localized to chromosome q24-q26 of chromosome 10 (T. L. Yang-Feng et al., *Proc. Natl. Acad. Sci.* (USA) 87:1516-1520 (1990)), while the intronless gene of $\beta_2$-AR has been localized to q31-q32 of chromosome 5. The human $\beta_1$-AR and $\beta_2$-AR are 477 amino acids and 413 amino acids long, respectively, and they are structurally similar in many respects.

The human heart expresses both $\beta_1$-AR and $\beta_2$-AR sub-types (M. R. Bristow et al., *Mol. Pharmacol.* 35:296-303 (1988)). Each receptor mediates positive inotropic and chronotropic responses to endogenous catecholamines and exogenously administered agonists (E. O. Brodde et al., *J. Cardiovasc. Pharmacol.* 8:1235-1242 (1986); O. E. Brodde et al., *Z. Kardiol.* 81:71-78 (1992)).

Thus, the administration of β-blockers provides the therapeutic benefit in heart failure. However, there is a very high degree of variability in the treatment response to these agents (M. M Givertz, *N. Engl. J. Med.* 342:1120-1122 (2000)). Further, tests to predict which patients will respond are not currently available, leading to a "trial-and-error" method to tailor the treatment to the patient, and thus ultimately suboptimal care is provided. Thus, there is a need in the art for improved methods to identify these polymorphisms and to correlate the identity of these polymorphisms with functions of β-adrenergic receptors. The present invention addresses these needs and more by providing polymorphisms, molecules, and methods useful for the diagnosis or risk assessment, predicting relative efficacy of β blocker therapy, and prognosis of cardiovascular diseases, obesity, and diabetes.

SUMMARY OF THE INVENTION

The present invention is directed to molecules useful for determining the identity of one or more polymorphic sites in the $\beta_1$- and $\beta_2$-adrenergic receptors ($\beta_1$-AR and $\beta_2$-AR) genes. The invention is also directed to methods for determining the identity of one or more polymorphic sites in the $\beta_1$-AR and $\beta_2$-AR genes. In particular, the invention is directed to molecules and methods useful for determining the identity of one or more polymorphic sites in the $\beta_1$-AR and $\beta_2$-AR genes and correlating the identity of such sites with a genetic predisposition for a disease. The invention is particularly concerned with a genetic predisposition for cardiovascular diseases including hypertension, congestive heart failure, stroke, myocardial infarction, neurogenic and obstructive peripheral vascular disease, and migraine, as well as a genetic predisposition for obesity and diabetes.

The invention also provides a kit, suitable for genetic testing. Such a kit contains primers for amplifying regions of β-AR nucleic acid encompassing regions where at least one of the polymorphisms are found. The kit also contains allele-specific oligonucleotides, specific for both mutant and wild-type alleles of at least one of these mutations. The kit may also contain sources of control target polynucleotides, as positive and negative controls. Such sources may be in the form of patient nucleic acid samples, cloned target polynucleotides, plasmids or bacterial strains carrying positive and negative control DNA.

In one aspect, the invention provides an oligonucleotide for determining the identity of a polymorphic site of a $\beta_1$-AR molecule of a target polynucleotide, wherein: a) said target polynucleotide comprises a segment of a of a $\beta_1$-AR molecule; b) said segment comprises said polymorphic site; and c) said oligonucleotide is complementary to said segment.

The invention particularly concerns the embodiments wherein said oligonucleotide comprises said polymorphic site, and said oligonucleotide is an allele-specific oligonucleotide or wherein said oligonucleotide does not comprise said polymorphic site, and said oligonucleotide is a primer oligonucleotide.

The invention further provides such an allele-specific oligonucleotide, wherein said oligonucleotide is complementary to said target polynucleotide at a region comprising or being nucleotide position 145 or 1165 of a coding region of the $\beta_1$-AR molecule.

The invention further concerns the embodiment in which such oligonucleotide is labeled with a label selected from the group: radiolabel, fluorescent label, bioluminescent label, chemiluminescent label, nucleic acid, hapten, or enzyme label.

The invention further provides a primer oligonucleotide for amplifying a region of a target polynucleotide, said region comprising a polymorphic site of a $\beta_1$-AR, wherein said primer oligonucleotide is substantially complementary to said target polynucleotide, thereby permitting the amplification of said region of said target polynucleotide.

In another aspect, the invention provides methods of predicting relative risk of a subject developing heart failure, or of predicting relative survival rate in a subject with heart failure, where a sample comprising a polynucleotide encoding a $\beta_1$-adrenergic receptor molecule or fragment of the polynucleotide from the subject is obtained and the sample is analyzed for a polymorphic site at nucleotide position 1165 of the polynucleotide or fragment of the polynucleotide, wherein a polypeptide with an arginine at position 389 is produced and indicates a decreased survival rate, thereby determining survival rate in the subject with congestive heart failure. The invention also encompasses methods in which proteins, rather than nucleic acids are analyzed to identify the polymorphism. In other aspects, the invention provides methods of predicting relative risk of a subject developing heart failure, or of predicting relative survival rate in a subject with heart failure that includes, in addition to analysis of the $\beta_1$-adrenergic receptor polymorphism, analysis of an $\alpha_{2c}$-adrenergic receptor polymorphism. Especially preferred is analysis of the del322-325 polymorphism described in Small, et al., New Engl. J. of Med. 347:1135-1142 (Oct. 10, 2002), and in U.S. Patent Publication No. 20030113725 the entire contents of which are herein incorporated by reference in their entirety.

In another aspect, the invention provides methods of predicting the relative efficacy of beta blocker therapy in a patient the presence of a $\beta_1$-adrenergic receptor polymorphism is determined, wherein the polymorphism comprises Arg389; and predicting that the beta blocker therapy will be efficacious in the patient if the polymorphism is present. The presence of the polymorphism in a patient is diagnostic or predictive of the relative risk for developing a cardiovascular disease, such as heart failure.

In another aspect, the invention provides methods of predicting the relative efficacy of beta blocker therapy in a patient, where the presence of a $\beta_1$-adrenergic receptor polymorphism, such as Arg389, is determined, and predicting that the beta blocker therapy will be relatively more efficacious in the patient if the polymorphism is present than if it is absent. The patient may be diagnosed with a cardiovascular disease, such as heart failure. The beta blocker therapy may comprise administering a drug selected from the group consisting of carvedilol, metoprolol, bisoprol and propranolol. In another aspect, the presence of C at position 1165 of the nucleic acid sequence encoding the $\beta_1$-adrenergic receptor is determined to predict the relative efficacy of beta blocker therapy.

In another aspect of the invention, transgenic animals whose genome comprises at least one transgene comprising a nucleic acid sequence encoding a polymorphism of $\beta_1$-adrenergic receptor are provided. The transgenic animal can be a mouse, and the polymorphism is a C at position 1165 of the nucleic acid sequence encoding the $\beta_1$-adrenergic receptor. In one aspect, the transgenic animal has an increase expression of a polypeptide having Arg389.

In yet another aspect of the invention, methods for testing a compound suspected of ameliorating cardiovascular disease are provided, where the methods comprise a mammalian cell to which is administered the compound; and the phenotype of the cell is monitored. In one aspect, the cardiovascular disease is heart failure, and the mammalian cell is a transgenic cell that comprises a nucleic acid sequence encoding a polymorphism of $\beta_1$-adrenergic receptor.

These and other aspects of the present invention will become evident upon reference to the following detailed description.

BRIEF DESCRIPTION OF DRAWINGS

FIG. 1b shows the expression of Ventricular G$\alpha_s$ and type 5 adenylyl cyclist (ACV) was reduced in Arg389 compared with Gly389 transgenic hearts. GRK-2 and G$\alpha_i$ were increased in hearts from both lines of transgenic mice, with no evidence of differential regulation by $\beta_1$-AR genotype. NTG denotes nontransgenic mice.

FIG. 3a shows that the dose of carvedilol did not differ between those of two homozygous genotypes. FIG. 3b shows that the improvement in LVEF was associated with $\beta_1$-AR position 389 genotype with homozygous Arg patients having a greater increase than those homozygous for Gly.

DETAILED DESCRIPTION

I. Definitions

Figure 1:
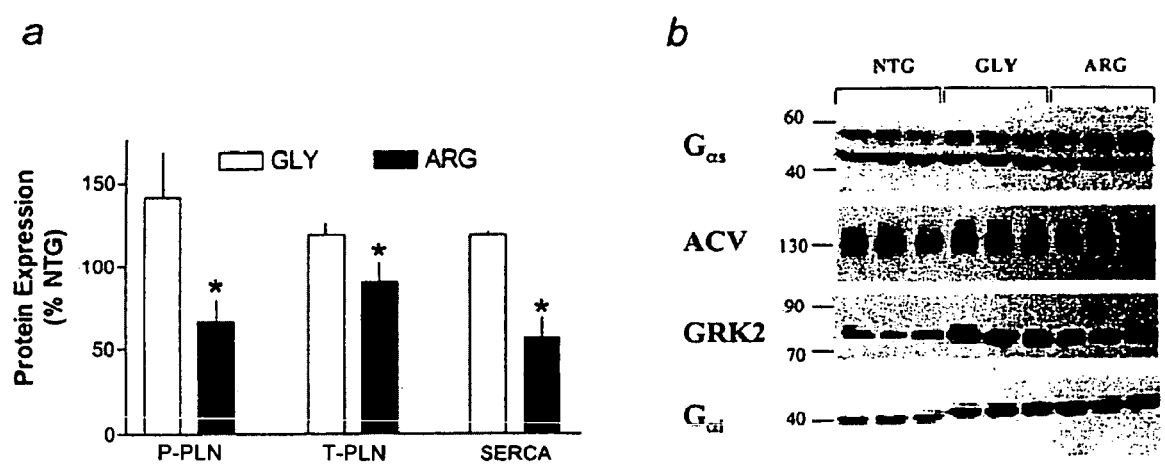
FIG. 1 illustrates the altered expression of calcium-cycling and $\beta_1$-AR signaling proteins in 6 month old Arg389 hearts. In 1a, phosphorylated PLN (P-PLN), total PLN (T-PLN) and SERCA-2a were reduced in ventricular membranes from Arg389 compared with Gly389 mice.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations arising with hosts that produce the proteins or errors due to PCR amplification.

As used herein, an "analogue" or "derivative" is a compound, e.g., a peptide, having more than about 70% sequence but less than 100% sequence similarity with a given compound, e.g., a peptide. Such analogues or derivatives may be comprised of non-naturally occurring amino acid residues, including by way of example and not limitation, homoarginine, ornithine, penicillamine, and norvaline, as well as naturally occurring amino acid residues. Such analogues or derivatives may also be composed of one or a plurality of D-amino acid residues, and may contain non-peptide interlinkages between two or more amino acid residues.

As used herein, the terms "label", "detectable label", and "reporter molecule" refer to a molecule capable of being detected, including, but not limited to, radioactive isotopes, fluorescers, chemiluminescers, chromophores, magnetic resonance agents, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range.

The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. For example, an "effective amount" for therapeutic uses is the amount of the composition comprising an oligonucleotide disclosed herein required to provide a clinically significant decrease in the symptoms of a cardiovascular disease, such as those resulting from a heart attack, for example. An appropriate "effective" amount in any individual case may be determined by one of ordinary skill in the art using routine experimentation.

As used herein, the terms "treat" or "treatment" are used interchangeably and are meant to indicate a postponement of development of a cardiovascular disease and/or a reduction in the severity of such symptoms that will or are expected to develop. The terms further include ameliorating existing symptoms, preventing additional symptoms, and ameliorating or preventing the underlying metabolic causes of symptoms.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention. Low stringency hybridization and annealing conditions permit the annealing of complementary nucleic acids that contain mismatched nucleic acids. As the stringency is raised, annealing of sequences containing mismatched nucleic acids is disfavored. Conditions which result in low or high stringency levels are known in the art (e.g., increasing the annealing temperature raises the stringency). Hybridizations are usually performed under stringent conditions, for example, at a salt concentration of no more than 1M and a temperature of at least 25° C. For example, conditions of 5× SSPE (750 mm NaCl, 50 mM NaPhosphate, 5 mM EDTA, pH 7.4) and a temperature of about 25° C. to 30° C. are suitable for allele-specific probe hybridizations.

"Homology" refers to the percent similarity between two polynucleotide or two polypeptide moieties. Two DNA, or two polypeptide sequences are "substantially homologous" to each other when the sequences exhibit at least about 50%, preferably at least about 75%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=5 0 sequences; sort by=HIGH SCORE; Databases=non-redundant, GenBanik+EMBL+DDBJ+PDB+GenBanik CDS translations+Swiss protein+Spupdate+PIR. Details of these programs can be found at the National Center for Biotechnology Information website via the link to BLAST or Basic Local Alignment Search Tool.

The above-referenced methods for determining homology also may be used to align similar sequences and so identify corresponding positions in two or more sequences (nucleic acid or polypeptide sequences). The two or more sequences may represent splice variants or homologous sequences from different species. While the polymorphisms of the present invention have been described by reference to the coding sequence of particular molecules such as, e.g., the human $\beta_1$-adrenergic receptor as described in GenBank Accession number AF 16900 and in Mason, Moore, Green, and Liggett, "A gain-of-function polymorphism in a G-protein coupling domain of the human beta1-adrenergic receptor," J. Biol. Chem. 274(18),12670-12674 (1999) (both of which are herein incorporated by reference in their entirety), one of ordinary skill will readily recognize that the invention is intended to encompass polymorphisms occurring in corresponding positions in different sequences.

Alternatively, homology can be determined by hybridization of polynucleotides under conditions which form stable duplexes between homologous regions, followed by digestion with single-stranded-specific nuclease(s), and size determination of the digested fragments DNA sequences that are substantially homologous can be identified in a Southern hybridization experiment under, for example, stringent conditions, as defined for that particular system. Defining appropriate hybridization conditions is within the skill of the art.

The term "wild type" as used herein in reference to a gene, nucleic acid or gene product, especially a protein and/or biological property, denotes a gene, gene product, protein, or biological property predominantly found in nature.

The term "transgenic animal" refers to an animal that contains within its genome a specific gene that has been disrupted or altered. The transgenic animal includes both the heterozygote animal (i.e., one defective allele and one wild-type allele) and the homozygous animal (i.e., two defective alleles).

The term "polymorphism" as used herein refers to the occurrence of two or more genetically determined alternative sequences or alleles in a population. A single nucleotide polymorphism occurs at a polymorphic site occupied by a single nucleotide, which is the site of variation between allelic sequences. A single nucleotide polymorphism usually arises due to substitution of one nucleotide for another at the polymorphic site. Single nucleotide polymorphisms can also arise from a deletion of a nucleotide or an insertion of a nucleotide relative to a reference allele.

The term "allele-specific oligonucleotide" refers to an oligonucleotide that is able to hybridize to a region of a target polynucleotide spanning the sequence, mutation, or polymorphism being detected and is substantially unable to hybridize to a corresponding region of a target polynucleotide that either does not contain the sequence, mutation, or polymorphism being detected or contains an altered sequence, mutation, or polymorphism.

As used herein, the term "cardiovascular disease" has its art-recognized meaning, which includes hypertension, congestive heart failure, stroke, myocardial infarction, neurogenic peripheral vascular disease, obstructive peripheral vascular disease, and migraine. The molecules of the present invention are preferably used in conjunction with the methods of the present invention, which are discussed in detail below.

The molecules of the present invention will preferably be "biologically active" with respect to either a structural attribute, such as the capacity of a nucleic acid to hybridize to another nucleic acid molecule or to be used by a polymerase as a primer. Alternatively, such an attribute may be catalytic, and thus involve the capacity of the agent to mediate a chemical reaction or response.

II. Overview

The present invention discloses methods, compositions, and kits for determining predisposition to cardiovascular diseases, and for predicting the efficacy of $\beta$-blockers in the treatment of a patient.

In one aspect, the invention relates to methods and compositions for the treatment and diagnosis of cardiovascular diseases. In particular, the present invention identifies and describes polymorphic variations in the human $\beta_1$-AR gene at nucleotide 1165 of the coding region. The resulting polypeptides have either an Arg or Gly amino acid at position 389. The polymorphic variations can be used to assess the risk of cardiovascular diseases, such as heart failure, for the identification and therapeutic use of compounds as treatments of cardiovascular disease, for the diagnostic monitoring of patients undergoing clinical and/or preclinical evaluation for the treatment of cardiovascular disease, and for monitoring the efficacy of compounds in clinical trials, and for predicting the relative efficacy of beta blocker therapies. Further, the present invention describes methods for the diagnostic evaluation and prognosis of various cardiovascular diseases, and for the identification of subjects exhibiting a predisposition to such conditions. In addition, the invention provides transgenic animals expressing polymorphic human $\beta_1$-AR, and the use of the transgenic animals for allele-specific responses to therapeutic agents.

III. Polymorphisms of the Present Invention

The particular gene sequences of interest to the present invention comprise "mutations" or "polymorphisms" in the genes for the $\beta$-1-adrenergic receptor ($\beta_1$-AR), the $\beta$-2-adrenergic receptor ($\beta_2$-AR), and the $\alpha_2$c-adrenergic receptor ($\alpha_2$c-AR).

The terms "β-1-adrenergic receptor" polymorphisms or "β₁-AR" polymorphisms refer to polymorphisms in the nucleic acid or amino acid sequence of a β₁-AR gene or gene product. For reference purposes only, GenBank Accession No. J03019 is an example of a wild-type β₁-AR gene sequence. For the purposes of identifying the location of a polymorphism, the first nucleotide of the start codon of the coding region; (the adenine of the ATG in a DNA molecule and the adenine of the AUG in an RNA molecule) of the β₁-AR gene is considered nucleotide "1." Similarly, the first amino acid of the translated protein product (the methionine) is considered amino acid "1."

Similarly, the terms "β₂-adrenergic receptor" polymorphisms or "β₂-AR" polymorphisms refer to the polymorphisms in the nucleic acid or amino acid sequence for the 2-AR gene or gene product. For reference purposes only, GenBank Accession No. M15169 is an example a wild-type β₂-AR gene sequence. For the purposes of identifying the location of a polymorphism, the first nucleotide of the start codon of the coding region (the adenine of the ATG in a DNA molecule and the adenine of the AUG in an RNA molecule) of the β₂-AR gene is considered nucleotide "1." Similarly, the first amino acid of the translated protein product (the methionine) is considered amino acid "1."

Similarly, the terms "α₂c-adrenergic receptor" polymorphisms or "α₂c-AR" polymorphisms refer to the polymorphisms in the nucleic acid or amino acid sequence for the α₂c-AR gene or gene product. For reference purposes only, GenBank Accession No. AF280399 is an example a wild-type α₂c-AR gene sequence. For the purposes of identifying the location of a polymorphism, the first nucleotide of the start codon of the coding region (the adenine of the ATG in a DNA molecule and the adenine of the AUG in an RNA molecule) of the α₂c-AR gene is considered nucleotide "1." Similarly, the first amino acid of the translated protein product (the methionine) is considered amino acid "1."

In addition to traditional nucleic acid or polypeptide sequencing and nucleic acid hybridization-based techniques, mass spectroscopy may be used to determine the presence or absence of polymorphisms. This is because the structure of molecules, such as peptides, proteins, receptors, antibodies, oligonucleotides, RNA, DNA, and other nucleic acids such as RNA/DNA hybrids, oligosaccharides, organic molecules and inorganic molecules, can be obtained using mass spectrometry. The mass spectrometry method can provide not only the primary, sequence structure of nucleic acids, but also information about the secondary and tertiary structure of nucleic acids, RNA and DNA, including mismatched base pairs, loops, bulges, kinks, and the like. The mass spectrometric techniques that can be used in the practice of the present invention include MSn (collisionally activated dissociation (CAD) and collisionally induced dissociation (CID)) and infrared multiphoton dissociation (IRMPD). A variety of ionization techniques may be used including electrospray, MALDI and FAB. The mass detectors used in the methods of this invention include FTICR, ion trap, quadrupole, magnetic sector, time of flight (TOF), Q-TOF, and triple quadrupole.

Electrospray ionization mass spectrometry (ESI-MS) is broadly applicable for analysis of macromolecules, including proteins, nucleic acids, and carbohydrates (Crain et al., Curr. Opin. Biotechnol. 9:25-34 (1998)). Fourier transform ion cyclotron resonance mass spectrometry (FT-ICR MS) can be used to resolve very small mass differences providing determination of molecular mass (Marshall, et al., Mass Spectrom. Rev. 17:1-35(1998)). In addition, Matrix-Assisted Laser Desorption/Ionization Mass Spectrometry (MALDI-MS) is another method that can be used for studying biomolecules (Hillenkamp et al., Anal. Chem. 63:1193A-1203A (1991)). In MALDI-MS high molecular weight biomolecules are ionized with minimal concomitant fragmentation of the sample material via the incorporation of the sample to be analyzed into a matrix that absorbs radiation from an incident UV or IR laser. This energy is then transferred from the matrix to the sample resulting in desorption of the sample into the gas phase with subsequent ionization and minimal fragmentation. MALDI spectra are generally dominated by singly charged species. Typically, the detection of the gaseous ions generated by MALDI techniques, are detected and analyzed by determining the time-of-flight (TO) of these ions. While MALDI-TOF MS is not a high resolution technique, resolution can be improved by making modifications to such systems, by the use of tandem MS techniques, or by the use of other types of analyzers, such as Fourier transform (FT) and quadrupole ion traps.

Fourier transform mass spectrometry (FTMS, Amster, J. Mass Spectrom. 31:1325-1337(1996)) can be used to obtain high resolution mass spectra of ions generated by any of the other ionization techniques. The basis for FTMS is ion cyclotron motion, which is the result of the interaction of an ion with a unidirectional magnetic field. The mass-to-charge ratio of an ion (m/q or m/z) is determined by a FTMS instrument by measuring the cyclotron frequency of the ion, and the detector can be used in conventional or tandem mass spectrometry, for the analysis of ions generated by a variety of different ionization methods including ESI and MALDI, or product ions resulting from collisionally activated dissociation (CAD).

Collisionally activated dissociation (CAD), also known as collision induced dissociation (CID), is a method by the ions of the molecules are dissociated by energetic collisions with neutral or charged species, resulting in fragment ions which can be subsequently mass analyzed. Mass analysis of fragment ions from a selected parent ion can provide certain sequence or other structural information relating to the parent ion, and is generally referred to as tandem mass spectrometry (MS or MS/MS).

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense) strand of a nucleic acid molecule is also intended to include the thymine (uridine), adenine, guanine, or cytosine (respectively) at the corresponding site on a minus (antisense) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

The polymorphic variation in the human β₁-AR gene at nucleotide 1165 of the coding region results in either Arg or Gly as the amino acid at position 389 of the polypeptide. The polypeptide with Gly389 is the minor allele and occurs with a frequency of approximate 25% to about 45%. Preferred polymorphisms and polymorphic sites in a gene for a β₁-AR gene include the following:

TABLE 1

β-Adrenergic Receptor Polymorphisms

| | Nucleotide position | Nucleotide | Amino acid position | Amino acid | Designations |
|---|---|---|---|---|---|
| β₁-AR | 1165 | G or C | 389 | Gly or Arg | $Gly^{389}$ or $Arg^{389}$ |
| β₁-AR | 145 | A or G | 49 | Ser or Gly | $Ser^{49}$ or $Gly^{49}$ |

IV. The Molecules of the Present Invention

The molecules of the present invention are particularly relevant to the diagnosis and prognosis of cardiovascular diseases, obesity, and diabetes.

A preferred class of molecules of the present invention comprise β-adrenergic receptor molecules. Preferably, β-adrenergic receptor molecules will be $\beta_1$-AR molecules or $\beta_2$-AR molecules. Such molecules may be either DNA or RNA, single-stranded or double-stranded. Such molecules may also be fragments, portions, and segments thereof and molecules, such as oligonucleotides, that specifically hybridize to β-AR nucleic acid molecules. Such molecules may be isolated, derived, or amplified from a biological sample. Alternatively, the molecules of the present invention may be chemically synthesized.

Oligonucleotides, such as primer oligonucleotides are preferably single stranded, but may alternatively be double stranded. If double stranded, the oligonucleotide is generally first treated to separate its strands before being used for hybridization purposes or being used to prepare extension products. Preferably, the oligonucleotide is an oligodeoxyribonucleotide. Oligonucleotides may be synthesized chemically by any suitable means known in the art or derived from a biological sample, as for example, by restriction digestion. The source of the oligonucleotides is not essential to the present invention. Oligonucleotides may be labeled, according to any technique known in the art, such as with radiolabels, fluorescent labels, enzymatic labels, proteins, haptens, antibodies, sequence tags, etc. Functional equivalents of nucleotides are those that act as a substrates for a polymerase as, for example, in an amplification method. Functional equivalents of nucleotides are also those that may be formed into a polynucleotide that retains the ability to hybridize in a sequence specific manner to a target polynucleotide.

Such oligonucleotides may be used as probes of a nucleic acid sample, such as genomic DNA, mRNA, or other suitable sources of nucleic acid. For such purposes, the oligonucleotides must be capable of specifically hybridizing to a target polynucleotide or β-AR nucleic acid molecule. As used herein, two nucleic acid molecules are said to be capable of specifically hybridizing to one another if the two molecules are capable of forming an anti-parallel, double-stranded nucleic acid structure under hybridizing conditions, whereas they are substantially unable to form a double-stranded structure when incubated with a non β-AR nucleic acid molecule under the same conditions. A nucleic acid molecule is said to be the "complement" of another nucleic acid molecule if it exhibits complete complementarity. As used herein, molecules are said to exhibit "complete complementarity" when every nucleotide of one of the molecules is complementary to a nucleotide of the other. Two molecules are said to be "substantially complementary" if they can hybridize to one another with sufficient stability to permit them to remain annealed to one another under at least conventional low-stringency conditions. Similarly, the molecules are said to be complementary if they can hybridize to one another with sufficient stability to permit them to remain annealed to one another under conventional high-stringency conditions. Departures from complete complementarity are therefore permissible, as long as such departures do not completely preclude the capacity of the molecules to form a double-stranded structure. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith for the purposes employed. However, for detection purposes, particularly using labeled sequence-specific probes, the primers typically have exact complementarity to obtain the best results.

Thus, for an oligonucleotide to serve as an allele-specific oligonucleotide, it must generally be complementary in sequence and be able to form a stable double-stranded structure with a target polynucleotide under the particular environmental conditions employed. Depending on the sequences being analyzed, one or more allele-specific oligonucleotides may be employed for each target polynucleotide. Preferably, allele-specific oligonucleotides will be completely complementary to the target polynucleotide. However, departures from complete complementarity are permissible.

In order for an oligonucleotide to serve as a primer oligonucleotide, however, it typically need only be sufficiently complementary in sequence to be able to form a stable double-stranded structure under the particular environmental conditions employed. Establishing environmental conditions typically involves selection of solvent and salt concentration incubation temperatures; and incubation times. The terms "primer" or "primer oligonucleotide" as used herein refer to an oligonucleotide as defined herein, which is capable of acting as a point of initiation of synthesis when placed under conditions in which synthesis of a primer extension product which is complementary to a nucleic acid strand is induced, as for example, in a PCR reaction. As with non-primer oligonucleotides, primer oligonucleotides may be labeled, according to any technique known in the art, such as with radiolabels, fluorescent labels, enzymatic labels, proteins, haptens, antibodies, sequence tags, etc.

In performing the methods of the present invention, the oligonucleotides or the target polynucleotide may be either in solution or affixed to a solid support. Generally, allele-specific oligonucleotides will be attached to a solid support, though in certain embodiments of the present invention allele-specific oligonucleotides may be in solution. In one aspect, the target polynucleotide is preferably bound to a solid support. The attachment may be either covalent or non-covalent. Attachment may be mediated, for example, by antibody-antigen-type interactions, poly-L-Lys, streptavidin or avidin-biotin, salt-bridges, hydrophobic interactions, chemical linkages, UV cross-linking, baking, and the like. In addition, allele-specific oligonucleotides may be synthesized directly on a solid support or attached to the solid support subsequent to synthesis. Preferably, the allele-specific oligonucleotides are affixed a solid support such that a free 3'-OH is available for polymerase-mediated primer extension.

Suitable solid supports for the present invention include substrates constructed of silicon, glass, plastic (polystyrene, nylon, polypropylene, etc.), paper, etc. Solid supports may be formed, for example, into wells (as in 96-well dishes), plates, slides, sheets, membranes, fibers, chips, dishes, and beads. In certain embodiments of the present invention, the solid support is treated, coated, or derivatized so as to facilitate the immobilization of an allele-specific oligonucleotide or a target polynucleotide. Preferred treatments include coating, treating, or derivatizing with poly-L-Lys, streptavidin, antibodies, silane derivatives, low salt, or acid.

V. Uses of the Polymorphisms and Molecules of the Present Invention

The polymorphisms and molecules of the present invention are preferably used in the diagnosis and prognosis of cardiovascular diseases, obesity, and diabetes. Alternatively, the polymorphisms and molecules of the present invention are used to predict an individuals responsiveness to synthetic agonists and antagonists, i.e., they may be used to assist in determining an appropriate treatment regimen for the above-mentioned diseases.

Quite apart from such usage, the polymorphisms and molecules of the present invention may be used to diagnose or predict an individual's sensitivity or responsiveness to administration of synthetic β-AR agonists and antagonists. Certain individuals exhibit a decreased responsiveness to such compounds (S. B. Ligget, In: The Genetics of Asthma, S. B. Ligget et al., eds. (1995)). The present invention can therefore be employed to diagnose or predict such sensitivity, as well as to guide selection of appropriate patient medication.

The Arg389 polymorphism may also dictate other therapeutic measures, based on the favorable response to b-blockers. In patients with bradycardia (normally a contraindication for β-blocker treatment) who also have the homozygous Arg389 polymorphism, a pacemaker can be implanted so that bradycardia is avoided yet the genetic advantage of the Arg389 genotype can be exploited by prescribing β-blockers.

Similarly, knowing the position 389 genotype can alter treatment with other agents. For example, in patients with the β 1-Gly389 genotype, where β-blockade has a lower probability of providing benefit, the dosage of an angiotensin converting enzyme inhibitor can be increased above recommended doses in order to achieve improved outcome, given that β-blocker is not prescribed due to the unfavorable genotype.

Preferably, the identity of at least one polymorphic site in a $\beta_1$-AR molecule is determined. Generally, in performing the methods of the present invention, the identity of more than one polymorphic site is determined. In some preferred embodiments, the identity of between about two and about six polymorphic sites is determined, though the identification of other numbers of sites is also possible. Preferably, at least one polymorphism in both a $\beta_1$-AR and a $\beta_2$-AR is identified. Alternatively, the identity of at least one polymorphism is determined in either a $\beta_1$-AR or a $\beta_2$-AR, but not both. Further, the identity of four polymorphic sites in a 2-AR and two polymorphic sites in a $\beta_1$-AR is determined. In additional embodiments, the identity of at least one polymorphism in an $\alpha_2$c-AR is determined, alone or in combination with one or more polymorphisms of either or both of the $\beta_1$-AR and the $\beta_2$-AR.

In another aspect of the invention, the polymorphisms and molecules of the present invention are utilized in determining the identity of at least one polymorphic site of a $\beta_1$-AR and/or a $\beta_2$-AR and/or an $\alpha_2$c-AR gene and using that identity as a predictor for the development of, or the clinical course of, at least one cardiovascular disease. Examples of cardiovascular diseases include hypertension, congestive heart failure, stroke, myocardial infarction, neurogenic and obstructive peripheral vascular disease, and migraine. The invention is additionally directed to the use of $\beta_1$-AR and/or $\beta_2$-AR and/or $\alpha_2$c-AR polymorphisms as predictors of the development of, or the clinical course of, obesity and/or diabetes.

V. Cell- and Animal-based Model Systems

Described herein are cell- and animal-based models for cardiovascular disease. These models may be used, for example, to further characterize differentially expressed human $\beta_1$-AR gene and its polymorphs or in screening assays to identify compounds which are capable of ameliorating cardiovascular disease symptoms. Thus, the animal- and cell-based models may be used to identify drugs, pharmaceuticals, therapies and interventions which may be effective in treating cardiovascular diseases, and to determine the toxicity and bioavailability where such data can be used to determine the in vivo efficacy of potential cardiovascular disease treatments.

In one aspect of the invention, animal-based models of cardiovascular disease are provided that include, but are not limited to, non-recombinant and engineered transgenic animals. Animal models exhibiting cardiovascular disease symptoms may be engineered by utilizing, for example, $\beta_1$-AR gene or either one of its polymorphs in conjunction with techniques for producing transgenic animals that are well known to those of skill in the art. For example, $\beta_1$-AR gene sequence can be introduced into, and overexpressed in, the genome of the animal of interest, or they may either be overexpressed or underexpressed.

In order to overexpress $\beta_1$-AR gene and its polymorphs, the coding portion of the $\beta_1$-AR gene sequence can be ligated to a regulatory sequence capable of driving gene expression in the animal and cell type of interest. Such regulatory regions are well known to those of skill in the art.

Animals of any species, including, but not limited to, mice, rats, rabbits, guinea pigs, pigs, micro-pigs, goats, and non-human primates, such as baboons, monkeys, and chimpanzees may be used to generate cardiovascular disease animal models.

Any technique known in the art may be used to introduce $\beta_1$-AR gene and its polymorphism transgenes into animals to produce the founder lines of transgenic animals. Such techniques include, but are not limited to pronuclear microinjection (U.S. Pat. No. 4,873,191); retrovirus mediated gene transfer into germ lines (Van der Putten et al., *Proc. Natl. Acad. Sci., USA* 82:6148-6152 (1985)); gene targeting in embryonic stem cells (Thompson et al., *Cell* 56:313-321 (1989)); electroporation of embryos (Lo, *Mol Cell. Biol.* 3:1803-1814 (1983)); and other techniques used in the art and reviewed in Gordon, *Intl. Rev. Cytol.* 115:171-229(1989).

Once transgenic animals have been generated, the expression of the recombinant $\beta_1$-AR gene and/or its allelic genes and proteins can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animals, in situ hybridization analysis, and RT-PCR, or evaluated immunocytochemically using antibodies specific for the gene product. Once the transgenic founder animals are produced, they may be bred, inbred, outbred, or crossbred to produce colonies of the particular animal.

In another aspect of the invention, cells that contain and express $\beta_1$-AR gene and its polymorphs gene sequences, and exhibit cellular phenotypes associated with cardiovascular disease, can be utilized to identify compounds that exhibit anti-cardiovascular disease activity. Such cells may include non-recombinant monocyte cell lines, such as U937 (ATCC No.: CRL-1593), THP-1 (ATCC No.: TIB-202), and P388D1 (ATCC No.: TIB-63); endothelial cells such as HUVEC's and bovine aortic endothelial cells (BAEC's); as well as mammalian cell lines such as HeLa cells and COS cells. Further, such cells may include recombinant, transgenic cell lines. For example, the cardiovascular animal models of the invention described in detail above, can be used to generate cell lines, containing one or more cell types involved in cardiovascular disease, that can be used as cell culture models for this disorder.

Alternatively, cells of a cell type known to be involved in cardiovascular disease may be transfected with sequences capable of increasing or decreasing the amount of $\beta_1$-AR gene and its polymorphism gene expression within the cell. For example, $\beta_1$-AR gene and its polymorphism gene sequences may be introduced into, and overexpressed in, the genome of the cell of interest, or, if endogenous target gene sequences are present, they may be either overexpressed or, alternatively disrupted in order to underexpress or inactivate target gene expression.

In another aspect of the invention, screening assays for compounds that interact with the $\beta_1$-AR gene and its polymorphism gene products and/or that modulate their gene expression are provided. Assays to identify compounds that bind to the products of $\beta_1$-AR gene or its polymorphs or bind to other cellular or extracellular proteins that interact with the products of $\beta_1$-AR gene and its polymorphs are provided. Compounds identified using such assays can ameliorate cardiovascular diseases, such as, for example, heart conditions, atherosclerosis, ischemia/reperfusion, hypertension, restenosis, and arterial inflammation by modulating the activity of the $\beta_1$-AR and its polymorphs. Such compounds include, but are not limited to peptides, antibodies, small organic compounds, or inorganic compounds. Compounds identified can be useful, for example, in modulating the activity of $\beta_1$-AR gene and/or its polymorphs, and the proteins products thereof.

Typically, a reaction mixture of $\beta_1$-AR and its polymorphs and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring the $\beta_1$-AR and/or its polymorphs or the test substance onto a solid phase and detecting protein/test substance complexes anchored on the solid phase at the end of the reaction. Normally, the test compound, which is not anchored, may be labeled, either directly or indirectly, although, alternatively, the protein can be labeled. In an alternative method, the reaction can be conducted in a liquid phase, the reaction products separated from unreacted components, and complexes detected; e.g., using an immobilized antibody specific for $\beta_1$-AR gene and its polymorphism gene product or the test compound to anchor any complexes formed in solution, and a labeled antibody specific for the other component of the possible complex to detect anchored complexes. The compounds thus identified can be screened for their ability to function as ligands, i.e., to bind to the receptor protein in a manner that triggers the signal transduction pathway.

In another aspect of the invention, methods for screening candidate compounds for their ability to antagonize the interaction between ligand and the receptor domain of $\beta_1$-AR gene and its polymorphs is provided. The method involves: a) mixing a candidate antagonist compound with a first compound which includes a recombinant $\beta_1$-AR gene and/or its polymorphism gene products comprising a receptor domain with a ligand; b) determining whether the antagonist or the ligand compounds bind; and c) identifying antagonistic compounds as those which interfere with the binding of the ligand.

The compounds that bind to $\beta_1$-AR and its polymorphs identified by the methods described above can be tested for the ability to ameliorate cardiovascular disease symptoms using cell-based and animal model-based assays.

In one aspect of the invention, cell-based models can be used to identify compounds that ameliorate cardiovascular disease symptoms. For example, such cell-based models can be exposed to a compound suspected of being able to ameliorate cardiovascular disease symptoms, at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype.

In another aspect, transgenic animals can be used to identify compounds capable of ameliorating cardiovascular disease symptoms. The animal models can be used to identify drugs, pharmaceuticals, therapies, and interventions which may be effective in treating cardiovascular disease. For example, animal models can be exposed to a compound suspected of being able to ameliorate cardiovascular disease symptoms, at a sufficient concentration and for a time sufficient to elicit such an amelioration of cardiovascular disease symptoms in the exposed animals. The response of the animals to the exposure can be monitored by assessing the reversal of disorders associated with cardiovascular disease, for example, by counting the number of atherosclerotic plaques and/or measuring their size before and after treatment.

In another aspect of the invention, the effects of the compounds on cardiovascular disease states, such as in clinical trials, can be monitored. Thus, in a clinical trial where the patients are administered the test drug, blood can be drawn from patients before and at different stages during treatment with such a drug. Their monocytes may then be isolated and RNA prepared and analyzed by differential display. The levels of expression of $\beta_1$-AR and/or its polymorphism genes can be quantified by Northern blot analysis or RT-PCR, or alternatively by measuring the amount of protein produced. Thus, these profiles can serve as surrogate markers indicative of the physiological response, and can be determined before, and at various points during, drug treatment.

In another aspect of the invention, antibodies that are specific for either $\beta_1$-AR or its polymorphs and interfere with their activity can be used to inhibit target gene function. Such antibodies can be generated against the proteins themselves or against peptides corresponding to portions of the proteins using standard techniques known in the art. Such antibodies include but are not limited to polyclonal, monoclonal, Fab fragments, single chain antibodies, chimeric antibodies, etc.

VI. Pharmaceutical Preparations and Methods of Administration

The methods described herein use pharmaceutical compositions comprising the molecules described above, together with one or more pharmaceutically acceptable excipients or vehicles, and optionally other therapeutic and/or prophylactic ingredients. Such excipients include liquids such as water, saline, glycerol, polyethyleneglycol, hyaluronic acid, ethanol, cyclodextrins, modified cyclodextrins (i.e., sufobutyl ether cyclodextrins) etc. Suitable excipients for non-liquid formulations are also known to those of skill in the art.

Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in *Remington's Pharmaceutical Sciences*, 18th Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, a softgel capsule or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile: injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

Alternatively, the pharmaceutical compositions of the invention may be administered in the form of suppositories for rectal or vaginal administration. These can be prepared by mixing the agent with a suitable nonirritating excipient which is solid at room temperature but liquid at the rectal temperature and therefore will melt in the rectum to release the drug. Such materials include cocoa butter, beeswax and polyethylene glycols.

Preferred formulations for topical drug delivery are ointments and creams. Ointments are semisolid preparations which are typically based on petrolatum or other petroleum derivatives. Creams containing the selected active agent, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the invention may also be delivered through the skin or muscosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or reservoir, underlying an upper backing layer. The laminated device may contain a single reservoir, or it may contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or gel reservoir, or may take some other form. The backing layer in these laminates, which serves as the upper surface of the device, functions as the primary structural element of the laminated structure and provides the device with much of its flexibility. The material selected for the backing layer should be substantially impermeable to the active agent and any other materials that are present.

As discussed above, the pharmaceutical formulations may contain one or more of the conjugates described above and additionally one or more active agents that effectively provide treatment for the subject. The additional active agent may be, but is not limited to, a 5-HT3 antagonist or agonist, a GABA antagonist or an agonist, a NSAID, 5-HT1A ligand, sigma receptor ligand, a COX-2 inhibitor, or another pain killer, a steroid, a vitamin, or a hormone, and combinations thereof. This additional active agent can be administered to the subject prior to, concurrently with or subsequently to administration of the compositions of this invention. Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention.

The compounds identified as inhibiting the gene expression of $\beta_1$-AR and its polymorphs, synthesis and/or activity of the receptors can be administered to a patient at therapeutically effective doses to treat or ameliorate cardiovascular disease. The toxicity and therapeutic efficacy of such compounds can be determined by standard pharmaceutical procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are normally preferred.

The data obtained from the cell culture assays and animal studies can be used in formulating a range of dosage for use in humans. The dosage preferably lies within a range of circulating concentrations that include the $ED_{50}$ with little or no toxicity. The dosage can vary within this range depending upon the dosage form employed and the route of administration utilized. The therapeutically effective dose can be determined from cell culture assays, and from animal models.

EXAMPLES

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Transgenic Mouse Model of $\beta_1$AR Polymorphisms and Effect on Cardiac Function Using the α-myosin heavy chain promoter, transgenic mice with targeted ventricular expression of the human $\beta_1$AR (Arg389 or Gly389 forms) were utilized to ascertain allele-specific cardiac function over time. Echocardiography was utilized to ascertain cardiac function in the intact mouse. At 3-months of age $\beta_1$-Arg389 mice and $\beta_1$-Gly389 mice had equivalent levels of cardiac function, as defined by ventricular fractional shortening: 43±2% vs 42±2% respectively. By 9-months of age, the $\beta_1$-Arg389 mice displayed dilated ventricles and a markedly decreased fractional shortening (26±2%) as compared to 9-month old β 1-Gly389 mice (42±4%, P=0.02). In addition, 9-month old $\beta_1$-Arg389 hearts had myocyte loss and replacement fibrosis as determined by light microscopy, while $\beta_1$-Gly389 hearts were normal.

Example 2

Response to β-Blockade in Transgenic Mice

Transgenic mice with targeted expression of $\beta_1$-Gly389 or $\beta_1$-Arg389 to the heart exhibit multiple alterations over time (observed as early as 6-months of age) in the expression of certain cardiac signaling and $Ca^{++}$ handling proteins. Expression levels of the two receptors were equivalent. 3-month-old mice of both genotypes, as well as nontransgenic mice, were treated with propranolol (0.5 mg/ml) in their drinking water, or water without propranolol (control) continuously for 6 months. Hearts were then removed and ventricular protein extracts prepared. These were subjected to Western blotting to ascertain expression of the proteins $G_{\alpha s}$, $G_{\alpha i2}$, G-protein coupled receptor kinase-2 (GRK2), adenylyl cyclase type 5 (AC5), total phospholamban (T-PLN), phosphorylated phospholamban (P-PLN) and sarcoplasmic endoplasmic reticulum calcium ATPase-2A (SERCA) using methods described in Perez et al. Nature Med 9: 1300-1305 (2003). Treatment effect was assessed by comparing expression of the proteins of untreated and propranolol treated mice, within genotype, by ANOVA. The data, shown in FIG. 1, shows that overall treatment response to propranolol was found only in hearts from the $\beta_1$-Arg389 mice.

Figure 2:
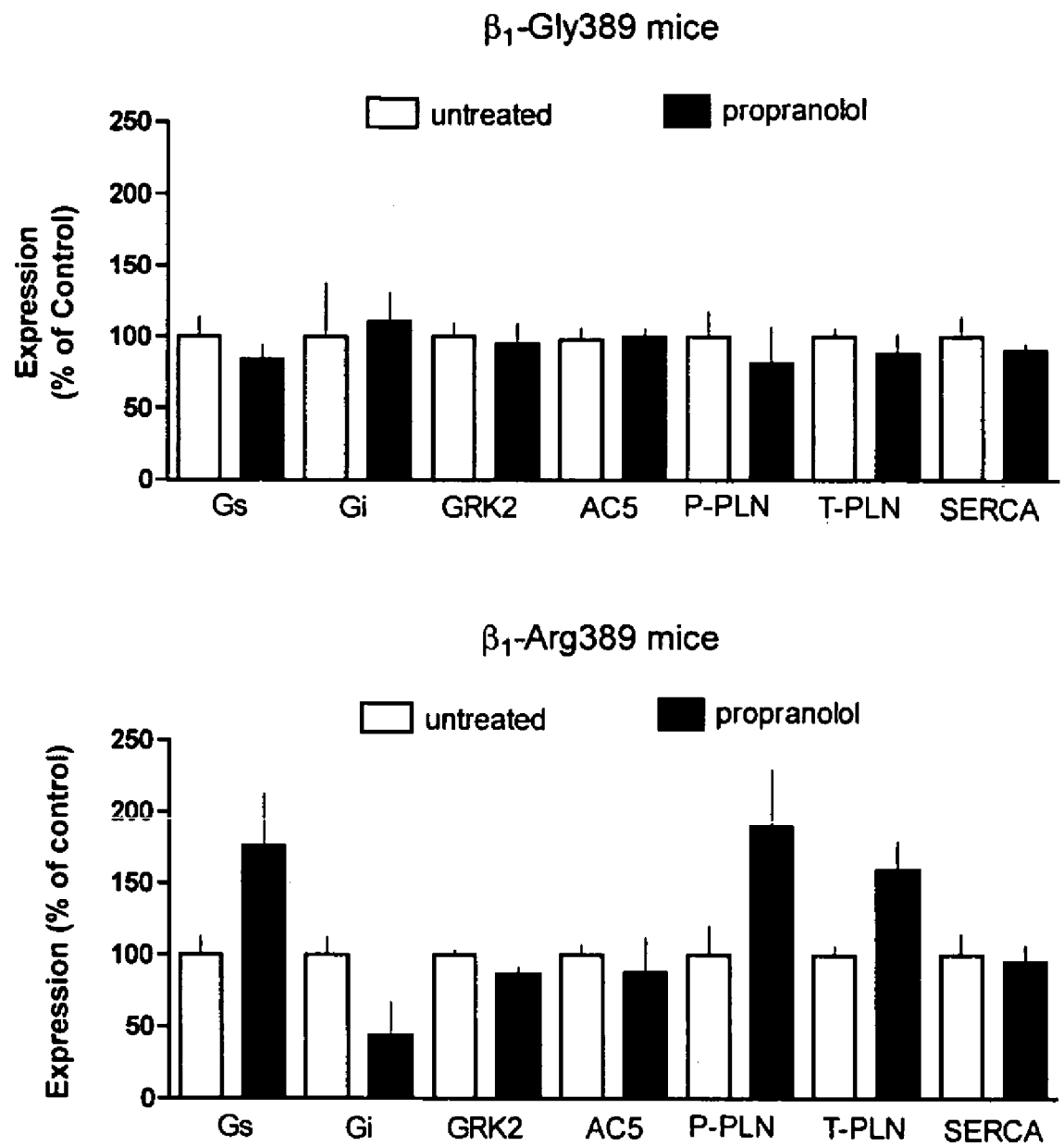
FIG. 2 illustrates the response to $\beta$-blockade in transgenic mice with targeted overexpression of Gly389 and Arg389 $\beta_1$-AR to the heart. Shown are mean (±SE) results from Western blots for the indicated proteins from hearts of $\beta_1$-Arg389 and $\beta_1$-Gly389 mice (n=3-4 in each group). Data are normalized to the control (untreated) values. An overall treatment response to propranolol was found only in hearts from the $\beta_1$-Arg389 mice (P<0.002 by ANOVA).

As shown in FIG. 2, propranolol treatment had no effect (P=0.67) on expression of the indicated proteins in hearts from Gly389 mice. In contrast, an overall treatment response (either increases or decreases in expression) was observed with propranolol treatment in hearts from Arg389 mice (P<0.002). The directions of these trends induced by β-blockade, which included increases in $G_{\alpha s}$, P-PLN and T-PLN, and decreases in $G_{\alpha i}$ and GRK2, are all considered restorative biochemical responses in the context of the hypertrophied/failing heart. Thus, the protein expression profiles associated with chronic α-blockade in this transgenic mouse model suggest that a relatively more favorable response to β-blockers is expected in $\beta_1$-Arg389 heart failure patients compared to those with the $\beta_1$-Gly389 genotype.

Example 3

Carvedilol Response by Genotype in Human Heart Failure.

Figure 3:
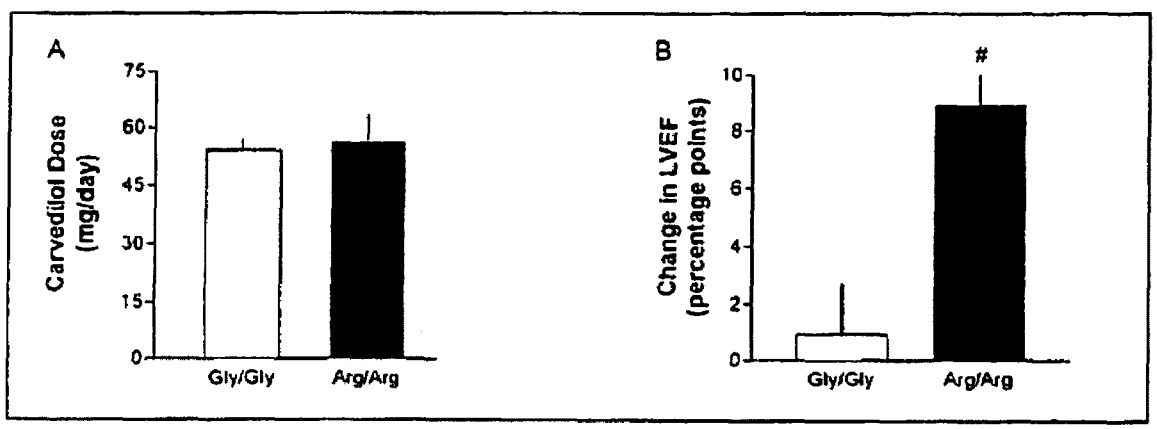
FIG. 3 illustrates the left ventricular ejection fraction (LVEF) response to carvedilol stratified by homozygous genotype.

The study was approved by the University of Cincinnati Institutional Review Board and the patients gave informed consent. Since the transgenic mice exhibited allele-specific response, the protective effects of β-blockade against chronic catecholamine stimulation of cardiac $\beta_1$-AR in human heart failure likely occurs in patients expressing the Arg389 variant. Thus, it is expected that a greater therapeutic response from Arg389 patients resulting in improvement in left-ventricular function (LVEF). 224, patients (ages 40-65) with ischemic or dilated cardiomyopathy and LVEF <35% were examined. The patients were treated with carvedilol using a standard up-titration dosing regiment. LVEF was determined by radionuclide ventriculography before initiation of drug treatment and after a maintenance period of >6 months on a stable dose. The change in LVEF was reported as the difference between values before and after drug treatment. Patients were genotyped at the $\beta_1$-AR 389 locus, and the distribution of the patient genotypes (16 Gly389 homozygotes, 95 Gly389/Arg389 heterozygotes and 144 Arg389 homozygotes) was in Hardy-Weinberg equilibrium. The ventricular function before treatment was not different between Arg389 and Gly389 homozygotes (LVEF of 26±8.60% v 25±0.9%, respectively). However, $\beta_1$-AR genotype was associated with improvement in LVEF. Arg389-homozygous patients showed greater improvement in LVEF (8.7±1.10%) compared with Gly389-homozygous patients (0.93±1.7%)(FIG. 3). Heterozygotes showed an improvement similar to that of Arg389-homozygous patients.

Thus, the Arg 389 variant predisposes a carrier to heart failure. Thus, $\beta_1$-AR genotyping of healthy patients and heart failure patients can be used to assess the risk or prognosis of cardiovascular diseases, and can be used to personalizing therapy.

Thus, the invention provides for treatment of heart failure by detecting and remediating (e.g., via conventional gene therapy techniques) the genomic polymorphism either systemically or in the affected tissues. Alternatively, such treatment may be attained through detection of the polymorphism or variant protein, and by application of appropriate medications, e.g., for blocking the adrenergic receptor.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

What is claimed is:

1. A method of predicting relative efficacy of a beta blocker therapy in a subject, the method comprising:
    determining from a sample from the subject the presence or absence of a polymorphism in a $\beta_1$-adrenergic receptor in the sample from the subject, wherein the polymorphism comprises arginine at position 389; and
    predicting relative efficacy of a beta blocker therapy, wherein the beta blocker therapy comprises administering carvedilol, based on the presence or absence of the polymorphism, the presence of the polymorphism indicating a relatively greater efficacy of the beta blocker therapy in the subject, wherein the subject is heterozygous or homozygous for the polymorphism, as compared to a subject lacking the polymorphism.

2. The method according to claim 1, wherein the subject was diagnosed with a cardiovascular disease before the determining step.

3. The method according to claim 2, wherein the cardiovascular disease is heart failure.

4. The method according to claim 1, wherein the determining step further comprises analyzing a nucleic acid in the sample.

5. The method according to claim 1, wherein the determining step further comprises analyzing a protein in the sample.

6. The method according to claim 4, wherein the analyzing comprises nucleic acid sequencing, restriction digestion, allele-specific polymerase reaction, allele-specific oligonucleotide hybridization, single-stranded conformational polymorphism analysis, genetic bit analysis, temperature gradient gel electrophoresis, ligase chain reaction, or ligase/polymerase genetic bit analysis.

7. The method according to claim 5, wherein the analyzing comprises contacting the protein with an antibody or fragment thereof, amino acid sequencing, or mass spectroscopy analysis.

8. The method according to claim 1 wherein efficacy of a beta blocker therapy comprises a measurable improvement in left ventricular ejection fraction.

* * * * *